United States Patent [19]

Cullen et al.

[11] Patent Number: 4,992,423
[45] Date of Patent: Feb. 12, 1991

[54] POLYCYCLIC ETHER ANTIBIOTICS

[75] Inventors: Walter P. Cullen, East Lyme, Conn.; Hiroshi Maeda, Aichi, Japan; John C. Ruddock, Canterbury, England; Junsuke Tone, Chita, Japan

[73] Assignee: Pfizer Inc., New York, N.Y.

[21] Appl. No.: 153,187

[22] Filed: Feb. 8, 1988

Related U.S. Application Data

[62] Division of Ser. No. 747,613, Jun. 21, 1985, Pat. No. 4,746,650.

[30] Foreign Application Priority Data

Jul. 12, 1984 [GB] United Kingdom ............... 8417785

[51] Int. Cl.$^5$ .................. A61K 31/71; C07H 17/04; C12P 17/18; A23G 3/00
[52] U.S. Cl. ................................ 514/27; 536/16.8; 536/18.7; 435/825; 426/658
[58] Field of Search ............... 514/27; 536/16.8, 18.1; 435/253; 426/658

[56] References Cited

U.S. PATENT DOCUMENTS 4,278,663 7/1981 Liu et al. ........................ 424/119
4,565,862 1/1986 Foley et al. ..................... 536/16.8

FOREIGN PATENT DOCUMENTS 0021170 2/1978 Japan .

Primary Examiner—John W. Rollins
Assistant Examiner—Elli Peselev
Attorney, Agent, or Firm—Peter C. Richardson; J. Trevor Lumb

[57] ABSTRACT

A new acidic polycyclic ether antibiotic UK-58,852 has the formula:

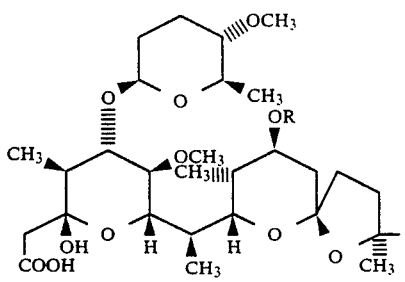

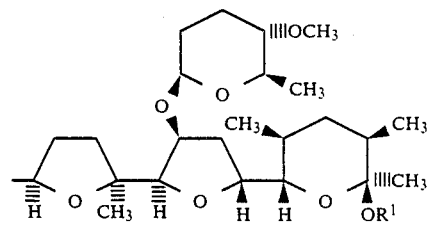

wherein R and $R^1$ are both hydrogen, and can be prepared by the submerged aerobic propagation in aqueous nutrient media of Actinomadura sp. ATCC 39697. The antibiotic and its cationic salts are active against a variety of microorganisms and are effective in controlling coccidiosis, enteritis, swine dysentery and theileriosis as well as being effective in promotion of growth and/or improving efficiency of feed utilization is swine and ruminants. Two minor components, where R is H and $R^1$ is $CH_3$ and wherein R and $R^1$ are both $CH_3$, have also been isolated from the fermentation.

5 Claims, No Drawings

POLYCYCLIC ETHER ANTIBIOTICS

CROSS-REFERENCE TO RELATED APPLICATIONS

This application is a division of application Ser. No. 747,613, filed June 21, 1985, now U.S. Pat. No. 4,746,650, issued May 24, 1988.

BACKGROUND OF THE INVENTION

This invention is concerned with new members of the acidic polycyclic ether group of antibiotics, a class of compounds characterized biologically by their effect on cation transport in mitochondria. This family of antibiotics includes such well known agents as monensin; nigericin; grisorixin; dianemycin; salinomycin; mutalomycin; ionomycin and leuseramycin. The subject has been reviewed by Westley, "Polyether Antibiotics", *Adv. Appl. Microbiol.*, 22, 177, 1977.

The polycyclic ether antibiotics listed above are active against Gram-positive bacteria, fungi and protozoa. In particular these antibiotics exhibit potent anti-coccidial activity. They have therefore been employed with varying degrees of success in the treatment of a variety of animal infections.

The well-known protozoan disease, coccidiosis, continues to be a serious problem and its control is of economic importance to veterinary science, especially to the poultry industry. Coccidiosis results from infection by one or more species of Eimeria or Isospora (for a summary, see Lund and Farr in "Diseases of Poultry," 5th ed., Biester and Schwarte, Eds., Iowa State University Press, Ames, Iowa, 1965, pp. 1056–1096). There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively innocuous; however, *E. mitis, E. hagani* and *E. praecox* are capable of reducing weight gain, lowering feed efficiency and adversely affecting egg production.

In view of the great economic losses due to coccidiosis and the known disadvantages of existing anti-coccidial agents, the search for better anticoccidial agents continues.

Enteritis is another disease which can cause severe economic losses to livestock producers. Enteritis occurs in chickens, swine, cattle and sheep and is attributed mainly to anaerobic bacteria, particularly *Clostridium perfringens*, and viruses. Enterotoxemia in ruminants, an example of which is "overeating disease" in sheep, is a condition caused by *C. perfringens* infection.

Swine dysentery is one of the most common swine diseases diagnosed in the United States. Additionally, the disease is prevalent in many other countries and annually causes considerable losses in stock to swine growers around the world. It has recently been discovered that a large spirochete is the causative organism of the disease. This organism, *Treponema hyodysenteriae*, has now been isolated and shown to be capable of producing the disease [Harris, D. L. et al. "Swine Dysentery-1, Inoculation of Pigs with *Treponema hyodysenteriae* (New Species) and Reproduction of the Disease," *Vet. Med/SAC*, 67, 61–64, 1972]. The test data recited hereinafter concerns tests conducted with this organism. It must be noted that it is not known whether *T. hyodysenteriae* is the sole causative organism of swine dysentery. From the data available, however, it can be concluded that it is a primary source of the infection.

Performance enhancement (increased rate of growth and/or increased efficiency of feed utilization) in ruminants such as cattle, and in monogastric animals such as swine, is another economically desirable objective of veterinary science. Of particular interest is improved performance achieved by increasing the efficiency of feed-utilization. The mechanism for utilization of the major nutritive portion of ruminant feeds is well known. Micro-organisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids. For a more detailed discussion, see Leng in "Physiology of Digestion and Metabolism in the Ruminant," Phillipson et al., Eds., Oriel Press, Newcastle-upon-Tyne, England, 1970, pp. 408–410.

The relative efficiency of volatile fatty acid utilization is discussed by McCullough in "Feedstuffs", June 19, 1971, page 19; Eskeland et al. in *J. An. Sci.*, 33, 282, 1971; and Church et al. in "Digestive Physiology and Nutrition of Ruminants", Vol. 2, 1971, pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilisation efficiency and also reducing the incidence of ketosis.

Yet another disease which causes economic losses to livestock producers is caused by the protozoan parasite *Theileria parva*. That disease, theileriosis, is also known as "East Coast fever", "Coastal fever" or "Rhodesian tick fever". The Theileria parasite invades but does not destroy red blood cells which gives rise to acute or chronic febrile infections. In cattle the disease is characterized by high fever, swelling of the lymph nodes, emaciation and high mortality. The disease is a very serious problem in East and Central Africa. See further "The Merck Veterinary Manual", Siegmund et al., Eds., Merck & Co., Rahway, N.J., 5th Ed., pp. 431–433 (1979).

SUMMARY OF THE INVENTION

This invention is concerned with a new acidic polycyclic ether antibiotic designated UK-58,852, produced by the submerged aerobic propagation in aqueous nutrient media of the microorganism *Actinomadura roseorufa* Huang sp. nov., ATCC 39697 isolated from a soil sample from Japan. The antibiotic and its cationic salts are active against a variety of microorganisms and are effective in controlling coccidiosis, enteritis, swine dysentery and theileriosis as well as being effective in promoting growth and increasing efficiency of feed utilisation in swine and ruminants. The invention also includes two related minor components produced in the fermentation (designated CP-70,228 and CP-70,828) which are also antibiotics effective in controlling coccidiosis. CP-70,228 is also useful in promoting growth and increasing efficiency of feed utilisation in swine and ruminants.

DETAILED DESCRIPTION OF THE INVENTION

The microorganism designated *Actinomadura roseorufa* Huang sp., nov., ATCC 39697, which is useful for the preparation of antibiotics UK-58,852, CP-70,228 and CP-70,828 was isolated from a soil sample collected in Izumo City, Shimane Prefecture, Japan. It was recognized to be an Actinomadura species because of the narrow dimensions of the hyphae, production of aerial mycelium, spores being borne in chains and presence of madurose in the whole-cell hydrolysates.

A culture thereof, designated herein as N596-33, was plants from a slant into ATCC no. 172 broth and grown for four days at 28° C. on a shaker. It was then centrifuged for 20 minutes, washed three times with sterile distilled water and planted on media commonly used for identification of members of the Actinomycetales as hereinafter described.

The culture was incubated at 28° C. and the results were read at varying times but most commonly were taken at 14 days. The colours are described in common terminology, but exact colours were determined by comparisons with colour chips from the *Colour Harmony Manual*, fourth edition. The methods of whole-cell amino acid and sugar analyses are those described in Becker et al., *Appl. Microbiol.*, 12, 421–423, 1964; and in Lechevalier, *J. Lab. Clin. Med.*, 71, 934–944, 1968.

Identification media used for the characterization of the culture and references for their composition or supplier are as follows:

1. Yeast Extract-Malt Extract Agar—(ISP medium no. 2, Difco).
2. Oatmeal Agar—(ISP medium no. 3, Difco).
3. Inorganic Salts-Starch Agar—(ISP medium no. 4, Difco).
4. Glycerol-Asparagine Agar—(ISP medium no. 5, Difco).
5. Czapek-Sucrose Agar—S. A. Waksman, The Actinomycetes, Vol. 2, medium no. 1, p. 328, 1961.
6. Glucose-Asparagine Agar—Ibid, medium no. 2, p. 328.
7. Bennett's Agar—Ibid, medium no. 30, p. 331.
8. Emerson's Agar—Ibid, medium no. 28, p. 331.
9. Nutrient Agar—Ibid, medium no. 14, p. 330.
10. Gordon and Smith's Tyrosine Agar—R. E. Gordon and M. M. Smith, *J. Bact.*, 69, 147–150, 1955.
11. Casein Agar—Ibid.
12. Calcium Malate Agar—S. A. Waksman, *Bact. Rev.* 21, 1–29, 1957.
13. Gelatin Agar—R. E. Gordon and J. M. Mihm, *J. Bact.*, 73, 15–27, 1957.
14. Starch Agar—Ibid.
15. Potato Carrot Agar—M. P. Lechevalier, *J. Lab. and Clinical Med.*, 71, 934–944, 1968, but use only 30 g potatoes, 2.5 g carrots and 20 g agar.
16. 2% Tap Water Agar.
17. Gauze's Mineral Medium no. 1—G. F. Gauze et al., Problems in the Classification of Antagonistic Actinomycetes. English Ed., p. 13, 1957.
18. Gauze's Organic Medium no. 2—Ibid.
19. Potato Dextrose Agar—Peel, cut up and steam 100 g. potatoes in 500 ml water, filter through cheese cloth, add 10 g. glucose, 50 ml coconut milk, 20 g. agar and enough water to make one liter.
20. Tryptone-Yeast Extract Broth—(ISP medium no. 1, Difco).
21. Peptone-Yeast Extract Iron Agar—(ISP medium no. 6, Difco).
22. Organic Nitrate Broth—R. E. Gordon and J. M. Mihm, *J. Bact.*, 73, 15–27, 1957.
23. Dextrose Nitrate Broth—S. A. Waksman, The Actinomycetes, Vol. 2, medium no. 1, p. 328, 1961, with 3 g dextrose substituted for 30 g sucrose and agar omitted.
24. Skim Milk—Difco.
25. Cellulose utilization—
    (a) H. L. Jensen, *Proc. Linn. Soc. N.S.W.*, 55, 231–248, 1930.
    (b) M. Levine and H. W. Schoenlein, A Compilation of Culture Media, medium no. 2511, 1930.
26. Carbohydrates—ISP medium no. 9, Difco; C-2 medium, H. Nonomura and Y. Ohara, *J. Ferment. Technol.*, 49 (11), 887–894, 1971.
27. Temperature Range—ATCC medium 172 in ATCC Culture Collection Catalogue, 15th ed., p. 608, 1982.

The observations of growth and appearance of the organism were as follows:

Yeast Extract-Malt Extract Agar—Growth good, white, with pink to pink-red tint (6ga, 6½ea, 6½ia), raised, wrinkled, aerial mycelium white; reverse pale yellowish to pink (2ea, 6ga); no soluble pigment.

Oatmeal Agar—Growth moderant, cream (1½ca), slightly raised, smooth; aerial mycelium none to sparse, white; reverse colourless to cream (1½ca); no soluble pigment.

Inorganic Salts-Starch Agar—Growth poor, colourless to pale cream (near 1½ca), thin, smooth; aerial mycelium none to sparse, white; reverse colourless to pale cream (near 1½ca); no soluble pigment.

Glycerol Asparagine Agar—Growth poor to moderate, colourless but pale pink (5ca) near the edge, thin but moderately raised near the edge, smooth; aerial mycelium none to sparse, white; reverse colourless to pale pink (5ca); no soluble pigment.

Czapek-Sucrose Agar—Growth moderate, pale pink, grayish yellow to red (5ca, 2gc, 6½ia), slightly raised, smooth; aerial mycelium none to sparse, visible only under the microscope; reverse same as surface; no soluble pigment.

Glucose-Asparagine Agar—Growth moderate to good, grayish yellow, yellowish brown to red (2ic, 3nc, 7½ia, 7½la), moderately raised, smooth, with a few small bumps; aerial mycelium none to sparse, white; reverse same as surface; soluble pigment cream (2ca).

Bennett's Agar—Growth good, grayish yellow (2gc, 2ie) with a pale pink edge (5ca), raised, wrinkled, with cracks in some areas; aerial mycelium none to sparse, white; reverse same as surface; soluble pigment grayish yellow (2ic).

Emerson's Agar—Growth good, pale yellowish, gray to dark brown (2gc, near gray series 3fe, 3li, 3ni), raised, wrinkled; aerial mycelium short, white; reverse dark brown to yellowish (3li, 4li, 2gc); soluble pigment yellowish (2lc).

Nutrient Agar—Growth moderate, orange (5ea, 5ga), thin to slightly raised, smooth; aerial mycelium none to sparse, white; reverse orange (5ga); no soluble pigment.

Gordon and Smith's Tyrosine Agar—Growth moderate to good, brown to dark brown (3le, 3lg, 3ni), moderately raised, smooth to slightly granular, with a crack in one streak; aerial mycelium none to sparse, white; reverse same as surface; soluble pigment yellowish brown (3lc).

Casein Agar—Growth moderate to good, pale pink (5ca, 5ea), slightly raised, smooth to wrinkled; aerial mycelium none or sparse near the edge, white; reverse pale yellowish to pale pink (2ca, 2ea, 5ca); soluble pigment yellowish brown (3lc).

Calcium Malate Agar—Growth moderate, cream (2ca) to white, appearing as isolated colonies, raised, smooth, aerial mycelium white; reverse cream (2ea, 2ca); no soluble pigment.

Gelatin Agar—Growth moderate, cream to dark yellowish (2ea, 2ic), slightly raised, smooth to slightly granular; aerial mycelium none to sparse, white; reverse pale yellowish (2ea); no soluble pigment.

Starch Agar—Growth moderate to good, cream (2ca, 2ea), moderately raised, smooth to slightly granular; aerial mycelium none to sparse, white; reverse cream (2ca, 2ea); no soluble pigment.

Potato Carrot Agar—Growth moderate, cream (2ca), slightly raised, smooth; aerial mycelium none to sparse, white; reverse cream (2ca); no soluble pigment.

Tap Water Agar—Growth poor, colourless to pale cream (1½ca), thin, smooth, no aerial mycelium; reverse colourless; no soluble pigment.

Gauze's Mineral Medium 1—Growth moderate, cream, yellowish green to pink-red (2ca, 1½gc, 1½ic, 5ca, 6ia, 6ga, 6la), thin, smooth, with a few spots of white aerial mycelium; reverse same as surface; no soluble pigment.

Gauze's Organic Medium 2—Growth moderate to good, pink-orange (4ea), moderately raised, smooth but slightly wrinkled near the edge; aerial mycelium short, white; reverse same as surface; no soluble pigment.

Potato Dextrose Agar—Growth good, dark yellowish, pink to red (2ic, 6ea, 6½nc), raised, wrinkled, aerial mycelium white to pink (6ea); reverse dark yellowish, red to dark red (2ic, 6½nc, 6½ni); soluble pigment pale yellowish (2ea).

Morphological Properties—The following morphological properties were observed on inorganic salts-starch agar after 21 days of incubation: spore mass in white colour-series; sporophores monopodially branched; spore chains flexuous or wavy, occasionally hooked, irregularly curved, or very loosely coiled up to 3 turns, 10 to 30 spores per spore chain; spores oval to elliptical, rarely globose, $1.1–1.6 \times 0.7–1.0$ μm or $0.7–1.0$ μm in diameter; warty, as revealed by scanning electron microscopy.

Biochemical Properties—Melanin not produced in tryptone-yeast extract broth; hydrogen sulfide not produced on peptone-yeast extract iron agar; gelatin liquefied; starch not hydrolyzed; nitrate reduced to nitrite in both organic nitrate broth and dextrose nitrate broth; no growth and no decomposition on both cellulose media; clearing and no coagulation on milk; casein digestion positive; digestion of calcium malate positive; tyrosine digestion weakly positive. Carbohydrate utilization was the same on ISP medium No. 9 and Nonomura and Ohara's C-2 medium: Glucose and rhamnose utilized; sucrose weakly utilized; fructose doubtfully utilized; arabinose, inositol, mannitol, raffinose and xylose not utilized.

Whole-Cell Analysis—The whole-cell hydrolysates contain meso-diaminopimelic acid, madurose, galactose, glucose, rhamnose and ribose.

Temperature Relations—The relationship of temperature to growth rate was observed to be as follows:

| 21° C. | 28° C. | 37° C. | 45° C. |
|---|---|---|---|
| Good growth | Good growth | Moderate to good growth | No growth |

The micro-organism is characterized by its inability to produce melanin, flexuous to wavy spore chains with warty spores, and presence of meso-diaminopimelic acid and madurose as whole-cell components. The aerial mycelium if produced is rudimentary and on some media is visible only under the microscope. The colour of aerial mycelium is white but may be pink on potato dextrose agar. The vegetative mycelium is distinctive, showing some shade of red on yeast extract-malt extract agar, Czapek-sucrose agar, glucose-asparagine agar, Gauze's organic medium no. 1 and potato dextrose agar. The culture fails to produce spores on most of the media used. On inorganic salts-starch agar, oatmeal agar and Gauze's mineral medium no. 1 they are produced in the form of a few, small, raised, white patches. The morphological and biochemical properties place the micro-organism in the genus Actinomadura. However the organism is different from any related species and represents a new species of the genus. It is herein designated as *Actinomadura roseorufa* Huang sp. nov. The specific epithet refers to the pink, pink-red, or red substrate mycelium of the culture. The culture thereof, N596-33, has been deposited with the American Type Culture Collection; 12301 Parklawn Drive, Rockville, Md. 20852, U.S.A. under the provisions of the Budapest Treaty on 24th May, 1984 under the Accession Number ATCC 39697.

Cultivation of *Actinomadura roseorufa* Huang sp. nov., ATCC 39697 and isolation of the Antibiotics UK-58,852, CP-70,228 and CP-70,828 may be conducted under conditions similar to those employed in previous fermentations yielding polyether antibiotics. See, for example, U.S. Pat. No. 4,361,649. Cultivation preferably takes place in aqueous nutrient media under submerged aerobic conditions with agitation at a temperature of 24° to 36° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles, fishmeal, cotton seed meal, and yeast extract as well as mineral salts such as sodium chloride and calcium carbonate and trace elements such as iron, magnesium, copper, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 200 cycles per minute whereas a fermentor is usually run at 300 to 1700 revolutions per minute. Aseptic conditions must, of course, be maintained through the transfer of the organism and throughout its growth.

Inoculum for the preparation of the antibiotics according to this invention may be obtained by employing growth from a slant of the culture or Roux bottles inoculated with the culture. A solid medium suitable for initial growth of the organism on slants and in Roux bottles is ATCC medium no. 172. The growth may be used to inoculate either shake flasks or inoculum tanks or the inoculum tanks may be seeded from the shake flasks. Growth in shaken flasks will generally have reached its maximum in 4 to 5 days whereas inoculum in submerged inoculum tanks will usually be in the most favourable period in 5 to 6 days.

The progress of antibiotic production during fermentation and the bioactivity of the fermentation broth can be monitored by biological assay of the broth employing a sensitive strain of *Staphylococcus aureus* or *Bacillus subtilis*. *B. subtilis* ATCC 6633 is a suitable strain for this purpose. Standard plate assay technique is employed in which the zone of inhibition surrounding a filter paper disc saturated with the broth is used as a measure of antibiotic potency. Also, thin-layer chromatography employing silica gel is a useful tool for detecting the antibiotics produced in fermentation media and analyzing the composition of crude and purified materials extracted from the fermentation broths. The chromatograms are developed with ethyl acetate and the antibiotic compounds are visualized by spraying with vanillin reagent and heating the TLC plate at 80° C. The developed plate can also be overlayed with agar seeded with either *S. aureus* or *B. subtilis* and incubated at 37° C. for 16 hours to visualize the antibiotics.

The Antibiotic UK-58,852 produced by fermentation of *Actinomadura roseorufa* Huang sp. nov., ATCC 39697 may be separated and recovered by extracting the whole, unfiltered fermentation broth with an organic solvent such as chloroform, ethyl acetate, methylisobutyl ketone or butanol at the naturally prevailing pH. Alternatively the mycelium can be separated after growth has been completed and the mycelium extracted with an organic solvent. The solvent extract can then be concentrated to a thin syrup and the pure antibiotic is obtained by chromatography.

The minor components CP-70,228 and CP-70,828 are recovered by further chromatography of the mother liquors.

A typical method of separation and recovery of the antibiotic compound of this invention is as follows:

The whole broth from fermentation of *Actinomadura roseorufa* Huang sp. nov., ATCC 39697 was extracted with methylisobutyl ketone. The solvent extract yielded a dark oil on solvent evaporation under vacuum. The oil was dissolved in hexane and poured onto a bed of silica gel. The silica gel bed was washed repeatedly with hexane and then eluted with chloroform, chloroform/ethyl acetate and ethyl acetate. The eluates were examined by thin-layer chromatography. Fractions containing the Antibiotic UK-58,852 were combined and evaporated to dryness. The product fraction may be further purified by crystallisation or by column chromatography if desired. Cycloserine is co-produced with the Antibiotic UK-58,852 but, because of its poor solvent solubility it does not interfere with the recovery of Antibiotic UK-58,852.

The minor components CP-70,228 and CP-70,828 are recovered by further elution of the column using a more polar solvent system. The crude products may be purified by further chromatography as necessary. In addition, the antibiotic CP-70,228 is produced when the free acid form of UK-58,852 is allowed to stand in methanol solution.

The antibiotic compounds of this invention are acidic, and will form cationic salts by reaction with basic agents. All such salts are within the scope of this invention. These salts are prepared by conventional methods for polyether (ionophore) antibiotics. In one method, a solution of the antibiotic in a volatile, water immiscible, organic solvent is washed with an aqueous solution containing at least a stoichiometric equivalent, and preferably a large excess, of an appropriate basic agent. After drying the organic solvent it is evaporated in vacuo to give the desired cationic salt. Typical basic agents which can be used for this purpose include alkali metal hydroxides, such as sodium hydroxide and potassium hydroxide, alkaline earth metal hydroxides, such as calcium hydroxide and barium hydroxide, and ammonium hydroxide.

X-ray analysis of the silver salt of Antibiotic UK-58,852 and analytical and spectral data for CP-70,228 and CP-70,828 indicates that the compounds have the following structure:

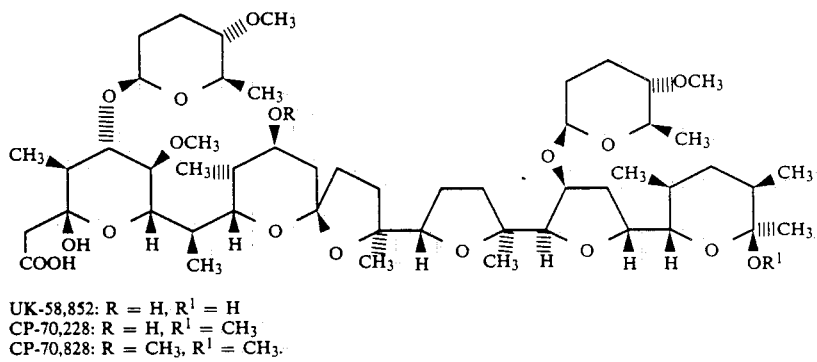

UK-58,852: R = H, R$^1$ = H
CP-70,228: R = H, R$^1$ = CH$_3$
CP-70,828: R = CH$_3$, R$^1$ = CH$_3$.

Antibiotic UK-58,852 exhibits inhibitory action against the growth of a number of Gram-positive microorganisms. In Table I, below, the results of in vitro tests are summarized. For this test each organism is inoculated in a series of test tubes containing nutrient medium and varying concentrations of Antibiotic UK-58,852 to determine the minimal concentration of the compound in mcg./ml. which inhibits the growth of the organism over a period of 24 hours (MIC).

TABLE I
ANTIBACTERIAL ACTIVITY

| Organism | Strain No. | MIC, mcg./ml. Antibiotic UK-58,852 (sodium salt) |
|---|---|---|
| Staphylococcus aureus | 01A005 | 3.12 |
|  | 01A052 | 3.12 |
|  | 01A110 | 3.12 |
|  | 01A400 | 6.25 |
| Streptococcus faecalis | 02A006 | >50 |
| Streptococcus pyogenes | 020303 | 0.05 |
| Actinomyces pyogenes | 14D011 | <0.08 |
| Actinobacillus pleuropneumoniae | 44B004 | >25 |
| Pasteurella multocida | 59A006 | >200 |
| Clostridium perfringens | 10A009 | 0.79 |
| Bacteroides fragilis | 78C024 | 0.10 |
| Fusobacterium necrophorum | 84C004 | >25 |
| Treponema hyodysenteriae | 94A007 | 0.39 |

Against the gram-negative bacteria such as *Escherischia coli, Pseudomonas aeruginosa, Klebsiella pneumoniae, Serratia marcescens* and *Enterobacteriaceae aerogenes*, MIC values were >50 in each case.

Antibiotic UK-58,852 and its cationic salts exhibit excellent activity against coccidial infections in poultry. When incorporated into the diet of chickens at levels of 25 to 150 ppm, these compounds are effective in controlling infections due to *Eimeria tenella, E. acervulina, E. maxima, E. brunetti* and *E. necatrix*.

Efficacy data for Antibiotic Compound UK-58,852 and its salts against coccidial infections in chickens was obtained in the following fashion. Groups of 3–5 ten-day old pathogen free white leghorn cockerel chicks were fed a mash diet containing Antibiotic UK-58,852 or its sodium and/or potassium salt uniformly dispersed therein. After being on this ration for 24 hours each chick was inoculated per os with oocysts of the particular species of Eimeria being tested. Other groups of 3–5 ten-day old chicks were fed a similar mash diet without Antibiotic UK-58,852 or its salts. They were also infected after 24 hours and served as infected controls. Yet another group of 3–5 ten-day old chicks were fed the same mash diet without Antibiotic UK-58,852 and were not infected with coccidia. These served as normal controls. The results of treatment were evaluated after five days in the case of *E. acervulina*, and six days for all other challenges.

The criteria used to measure anticoccidial activity consisted of lesion scores of 0 to 4 for *E. tenella* after J. E. Lynch, "A New Method for the Primary Evaluation of Anticoccidial Activity", *Am. J. Vet. Res.*, 22, 324–326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", *Exp. Parasit.*, 28, 30–36, 1970. A constant ratio was established by dividing the lesion score of each treated group by the lesion score of the infected control.

Table II summarizes the results obtained.

TABLE II
IN VIVO ANTICOCCIDIAL ACTIVITY

| INFECTION SPECIES | DOSE (PPM IN FEED) | AVERAGE DEGREE OF INFECTION | WEIGHT GAIN (PERCENT) |
|---|---|---|---|
| Eimeria tenella | 150 | 0.0 | 0 |
|  | 125 | 0.0 | 4 |
|  | 100 | 0.0 | 8 |
|  | 75 | 0.0 | 28 |
|  | 50 | 0.0 | 45 |
|  | 25 | 0.0 | 93 |
| Eimeria acervulina | 150 | 0.0 | 0 |
|  | 125 | 0.0 | 0 |
|  | 100 | 0.0 | 23 |
|  | 75 | 0.0 | 0 |
|  | 50 | 0.0 | 62 |
|  | 25 | 0.0 | 98 |

The value of animal feeds has generally been determined directly by feeding the animal. British Patent Specification No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content of the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml. added to a 50 ml. conical flask containing 400 mg. of standard substrate (68% corn starch+17% cellulose+15% extracted soybean meal), 10 ml. of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml. of the sample is mixed with 1 ml. of 25% metaphosphoric acid. After 10 minutes 0.25 ml. of formic acid is added and the mixture centrifuged at 1500 rpm for 10 minutes. Samples are then analyzed by gas-liquid chromatography by the method of D. W. Kellog, *J. Dairy Science*, 52, 1690, 1969. Peak heights for acetic, propionic and butyric acids are determined for samples from untreated and treated incubation flasks.

When tested by this in vitro procedure, Antibiotic UK-58,852 at the level of 10 micrograms per milliliter gave rise to an increase of about 93% in the production of propionic acid over that produced in the control solution without added Antibiotic UK-58,852. By comparison the commercially available compound salinomycin (another polycyclic ether antibiotic) at 10 mcg/ml. produced about an 88% increase of propionic acid over the control. In like manner, in a separate experiment, antibiotic CP-70,228 at a level of 10 mcg/ml. gave rise to an increase of about 30% in propionic acid production, as compared to an increase of about 40% using salinomycin at 10 mcg/ml.

These data show that Antibiotics UK-58,852 and CP-70,228 will improve feed utilisation by ruminants such as cattle and sheep. The compounds will also have a similar effect in monogastric animals such as pigs and rabbits. Antibiotics UK-58,852 and CP-70,228 may be incorporated in feed compositions as the free acid, sodium salt, potassium salt or mixtures thereof. Crude forms of Antibiotic UK-58,852 or CP-70,228, or dried fermentation broth containing the antibiotic, may also be incorporated in feed compositions at the desired potency concentrations.

The in vitro antibacterial activity of the minor antibiotic components CP-70,228 and CP-70,828 is summarized in Table III:

TABLE III

ANTIBACTERIAL ACTIVITY
MIC, mcg./ml.

| Organism | Strain No. | CP-70,228 Sodium Salt | CP-70,828 Sodium Salt |
|---|---|---|---|
| Staphylococcus aureus | 01A005 | 3.12 | 25 |
|  | 01A052 | 3.12 | 25 |
|  | 01A110 | 3.12 | 25 |
|  | 01A400 | 6.25 | 25 |
| Streptococcus faecalis | 02A006 | 50 | >50 |
| Streptococcus pyogenes | 020203 | 0.10 | 3.12 |
| Actinomyces pyogenes | 14D011 | 0.34 |  |
| Actinobacillus pleuropneumoniae | 54B004 | >100 |  |
| Pasteurella multocida | 59A006 | >100 |  |
| Clostridium perfringens | 10A009 | 1.58 |  |
| Bacteroides fragilis | 78C024 | 12.5 |  |
| Fusobacterium necrophorum | 84C004 | >100 |  |
| Treponema hyodysenteriae | 94A007 | 1.58 |  |

Against the gram-negative bacteria such as *Escherischia coli, Pseudomonas aeruginosa, Klebsiella pneumoniae, Serratia marcescens* and *Enterobacteriaceae aerogenes*, MIC values were >50 in each case.

Efficacy data for Antibiotic Compound CP-70,228 against coccidial infections in chickens following the procedures previously described is summarised in Table IV:

TABLE IV

IN VIVO ANTICOCCIDIAL ACTIVITY
CP-70,228

| INFECTION SPECIES | DOSE (PPM IN FEED) | AVERAGE DEGREE OF INFECTION | WEIGHT GAIN (PERCENT) |
|---|---|---|---|
| Eimeria tenella | 100 | 0.0 | 95 |
|  | 75 | 0.3 | 63 |
|  | 50 | 1.3 | 103 |
|  | 25 | 2.7 | 80 |
| Eimeria acervulina | 100 | 0.0 | 100 |
|  | 75 | 0.0 | 100 |
|  | 50 | 0.0 | 70 |
|  | 25 | 1.2 | 40 |

The invention is further illustrated by the following Examples.

EXAMPLE 1

1. Preparation of Inoculum

A sterile aqueous medium having the following composition was prepared.

| Ingredient | Grams/liter |
|---|---|
| Glucose | 20 |
| Soy Flour | 10 |
| NZ Amine YTT* | 5 |
| Sodium Sulphate | 0.5 |
| Cobalt Chloride | 0.002 |
| Calcium Carbonate | 2 |

One hundred ml of medium is distributed into 300 ml shake flasks and sterilized at 120° C. and 15 p.s.i. for 30 minutes. After cooling, the medium is inoculated with a vegetative cell suspension from a slant culture of Actinomadura sp. ATCC 39697 (N596-33).

The flasks are shaken at 28° C. on a rotary shaker having a displacement of 1½ to 2½ inches and 150 to 200 cycles per minute for three to five days.

The following medium was also employed with similar results.

| Ingredient | Grams/liter |
|---|---|
| Cerelose | 10 |
| Corn Starch | 5 |
| Corn Steep Liquor | 5 |
| NZ Amine YTT* | 5 |
| Cobalt Chloride | 0.002 |
| Calcium Carbonate | 3 |

*Registered trademark for enzymatic digest of casein, Humko Sheffield Chemical Co. Inc.

2. Fermentation and isolation of UK-58,852

A shake flask containing the grown culture was used to inoculate a five liter fermentation vessel containing three liters of sterile medium of the following composition to which 1 ml of silicone antifoaming agent had been added:

| Ingredient | Grams/liter |
|---|---|
| Cerelose | 10.0 |
| Corn Starch | 20.0 |
| NZ Amine YTT | 5.0 |
| Wheat Germ | 5.0 |
| Calcium Carbonate | 4.0 |
| Water to 1 liter |  |
| pH 6.9-7.0 |  |

Fermentation was carried out at 30° C. with stirring at 1700 revolutions per minute and aeration at one volume air per volume of broth per minute until substantial activity was observed (based on antibiotic disc assay versus *B. subtilis* ATCC 6633), usually 4-6 days. The bioactivity of the broth, and of subsequent recovery streams, were followed by using a sensitive strain of *Bacillus subtilis* ATCC 6633 or *Staphyloccocus aureus* ATCC 6538. The antibiotic component in the broth and recovery streams was visualized by using silica gel plates developed with ethyl acetate. The plates were sprayed with vanillin reagent (3 g vanillin in 75 ml ethanol and 25 ml 85% phosphoric acid) and heated at 80° C. Antibiotic UK-58,852 appears as an orange to red spot. Alternatively, the plate was overlayed with agar, seeded with either *S. aureus* or *B. subtilis*, to which 1.0 ml of a 1% solution of 2,3,5-triphenyl-2H-tetrazolium chloride had been added, and incubated at 37° C. for 16 hours to visualize the antibiotic as a white area against a pink background.

At the end of this time the whole broth was extracted with methylisobutyl ketone, the solvent separated and concentrated to yield 35 g residue. The residue was suspended in hexane and batch treated with silica gel on a filter funnel. The absorbant was washed with hexane, then eluted with chloroform, ethyl acetate and acetone. The activity was in the ethyl acetate fraction (20 g). This was concentrated, the residue rechromatographed on silica and the product crystallized from heptane to give Antibiotic UK-58,852 as a white solid (yield 80 mgs).

EXAMPLE 2

The procedure of Example 1 was followed but using the following medium for the fermentation:

| Ingredient | Grams/liter |
| --- | --- |
| Cerelose | 10 |
| Corn Starch | 5 |
| Corn Steep Liquor | 5 |
| Cobalt Chloride | 0.002 |
| NZ Amine YTT | 5 |
| Calcium Carbonate | 3 |

The whole broth of a 10 pot fermentation of a culture of *Actinomadura* sp. ATCC 39697 (total volume approximately 25 liters) was extracted with one third volume of methylisobutyl ketone. The extract was concentrated under vacuum to a brown oil (35 g). This material was chromatographed on a 5×100 cm column packed with column grade silica gel G (70–230 mesh, Woelm) in chloroform-acetone (3:1). The column was developed with chloroform-acetone (3:1) at a flow rate of 10 ml/min. Fractions of 10 ml each were taken.

The fractions were examined by thin-layer chromatography on Analtech silica gel GF plates developed in ethyl acetate. The plates were sprayed with 3% vanillin in ethanol-85% phosphoric acid (3:1) and heated to 80° C. The desired antibiotic UK-58,852 appears as a red spot under these conditions.

The fractions containing Antibiotic UK-58,852 were combined (total volume approximately 350 ml) and stirred with 2 grams of Darco G60 carbon for 5 minutes. The mixture was filtered and evaporated under vacuum. The yellow oil remaining after evaporation was dissolved in 100 ml of chloroform and stirred with an equal volume of water and the pH was adjusted to 4.0 with phosphoric acid. The phases were separated and the chloroform phase was stirred with an equal volume of 5% sodium phosphate dibasic buffer and the pH was adjusted to 9.0 with 1N sodium hydroxide solution. The phases were separated and the chloroform was dried over anhydrous sodium sulphate and then evaporated under vacuum. The yellow viscous oil remaining after evaporation was dissolved in a small volume of heptane whereupon crystallization occurred. The crystals were collected by filtration and dried under vacuum yielding 3.5 g of antibiotic UK-58,852 as the sodium salt; m.p. 182°–183° C. Found: C, 60.90; H, 8.32; $C_{52}H_{87}O_{18}Na$ requires C, 61.06; H, 8.51. Ultraviolet spectrum showed end absorption only. Optical rotation $[\alpha]_D = +10°$ (c=0.5, methanol). Infrared spectrum (KBr) cm$^{-1}$: 3423, 2966, 2928, 2869, 2821, 1613, 1453, 1407, 1377, 1361, 1312, 1257, 1238, 1206, 1175, 1160, 1116, 1093, 1064, 1030, 983, 969, 938, 919, 886.

The free acid form of Antibiotic UK-58,852 was prepared by stirring a chloroform solution of the sodium salt of UK-58,852 with an equal volume of water and lowering the pH to 3.0 with phosphoric acid. The phases were then separated, and the chloroform was evaporated under vacuum to give Antibiotic UK-58,852 as the free acid m.p. 123°–126° C. Ultraviolet spectrum showed end absorption only. Optical rotation $[\alpha]_D = +40°$ (c=0.5, chloroform).

EXAMPLE 3

A 1700 gallon fermentor, containing 1000 gallons of sterile medium of the following composition was inoculated with one liter of an inoculum of Actinomadura sp. ATCC 39697, prepared as described in Example 1.

| Fermentation Medium | |
| --- | --- |
| Ingredient | Grams/liter |
| Cerelose | 10 |
| Corn Starch | 5 |
| Corn Steep Liquor | 5 |
| Cobalt Chloride | 0.002 |
| NZ Amine YTT | 5 |
| Calcium Carbonate | 3 |

The fermentor was maintained at 28° C., with seration and stirring at 1700 revolutions per minute. After 296 hours the whole broth was extracted with 300 gallons, followed by 200 gallons of methylisobutyl ketone. The solvent extracts were separated combined and concentrated under vacuum to 10 liters of a brown oil. The extract was triturated by stirring with methanol for five minutes. The methanol phase was separated and the oil stirred with an additional 6 liters of methanol. The methanol fractions were combined and evaporated under vacuum (4 liters). One liter of this methanol concentrate was taken up in 2 liters of hexane and poured onto a bed of 3 kg of column grade silica gel in a Lapp filer. The silica gel was washed successively with hexane (11 liters), chloroform (7.5 liters) and finally ethyl acetate (7.5 liters). The fractions were examined by thin layer chromatrography. The product was found to be in the chloroform and ethyl acetate fractions. The chloroform and ethyl acetate fractions were both washed with water containing phosphoric acid to pH 4 and then with 5% sodium phosphate dibasic buffer (adjusted to pH 9.5 with 1N sodium hydroxide). The solvent fractions were then dried over anhydrous sodium sulphate and evaporated under vacuum. The oily residue remaining after evaporation was taken up in a small amount of hexane, whereupon crystallization occurred. The crystals were collected by filtration. The remaining 3 liters of methanol concentrate were treated as described above and the crystals obtained from all four runs were combined, yielding 300 g of Antibiotic UK-58,852 as the sodium salt.

EXAMPLE 4

Isolation of CP-70,228 from fermentation mother liquor 25 gm. of mother liquor from a UK-58,852 crystallization was chromatographed on a 50 mm×1 m column packed with column grade silica gel in a mixture of chloroform and acetone (4:1). The column was eluted at 10 ml/min with the same solvent, taking 10 ml fractions. Progress of the chromatography was monitored by thin layer chromatography. The UK-58,852 was contained in fractions 95-230. After 300 fractions 25% methanol was added to the system and elution was continued for an additional two liters. The CP-70,228 was contained in these fractions, which were evaporated to give 4.5 gm of a yellow oil. This material was further chromatographed on a 25 mm×50 cm column of Sephadex LH-20 in methanol. The flow rate was 1 ml/min and fractions were taken every 5 minutes. Fractions shown by thin layer chromatography to contain CP-70,228 were evaporated to give 1.3 g of a yellow oil. This concentrate was re-chromatographed on a 25 mm×50 cm column packed with column grade silica gel in chloroform containing 2.5% methanol. The column was run at 5 ml/min and fractions were taken every 2 minutes. Fractions shown by thin layer chromatography to contain CP-70,228 were combined and evaporated to yield 100 mg of white solid CP-70,228. m.p. 113°-123° C. Found: C,62.63; H,8.82. $C_{53}H_{90}O_{18}$ requires C,62.70; H,8.94%. Ultraviolet spectrum: no absorption. Optical rotation: $[\alpha]_D = +21.8°$ (c=0.5, methanol). Infrared spectrum (KBr) cm$^{-1}$: 3439, 2970, 2933, 2877, 1716, 1636, 1457, 1380, 1318, 1293, 1240, 1218, 1165, 1117, 1097, 1069, 1032, 989, 975, 940, 912, 897, 859.

EXAMPLE 5

Conversion of UK-58,852 to CP-70,228 Sodium Salt 11 gm of UK-58,852 free acid was dissolved in 200 ml of methanol and allowed to stand at room temperature. Thin layer chromatography of the solution after 1 hour showed complete conversion of the UK-58,852 to CP-70,228. The methanol was evaporated under vacuum and the concentrate was dissolved in 200 ml of chloroform. The chloroform, was stirred with 200 ml of 5% sodium phosphate dibasic buffer and the pH was adjusted to 10.5 with 6N sodium hydroxide. The phases were separated and the chloroform was dried over anhydrous sodium sulphate, filtered and evaporated under vacuum to an oil. 200 ml of heptane was added and the solution was again evaporated under vacuum, whereupon the CP-70,228 crystallized as the sodium salt. The salt was dried under high vacuum at 60° C. for 5 hours, yield 11 g. Spectral data and chromatography indicate that this material is identical to fermentation derived CP-70,228. m.p. 150°-155° C. Found: C,60.49; H,8.75. $C_{53}H_{89}O_{18}Na$ requires C,61.37; H,8.65%. Ultraviolet spectrum: no absorption. Optical rotation $[\alpha]_D = +13.6°$ (c=0.5, methanol). Infrared spectrum (KBr) cm$^{-1}$: 3429, 2973, 2935, 2878, 1594, 1455, 1399, 1379, 1319, 1291, 1268, 1242, 1215, 1189, 1165, 1117, 1096, 1068, 1030, 990, 975, 943, 891, 860, 833.

EXAMPLE 6

Isolation of CP-70,828 from fermentation mother liquor

The minor component CP-70,828 was isolated by repeated column chromatography of fermentation mother liquors. CP-70,828 was detected by vanillin spray in the same manner as CP-70,228. Single-spot (by tlc) CP-70,828 material was crystallized from heptane, yield 20 mg. m.p. 133°-136° C. Found: C,62.66; H,8.85. $C_{54}H_{92}O_{18}$ requires C,63.01; H,9.01%. Ultraviolet spectrum: no absorption. Infrared spectrum (KBr) cm$^{-1}$: 3416, 3259 (br), 2968, 2926, 2871, 1614, 1455, 1377, 1363, 1315, 1260, 1238, 1206, 1175, 1160, 1116, 1092, 1063, 1030, 986, 970, 939, 921, 887, 857, 827, 799, 661.

We claim:

1. A nutrient feed composition for cattle or swine characterized in that said feed contains the antibiotic of the formula

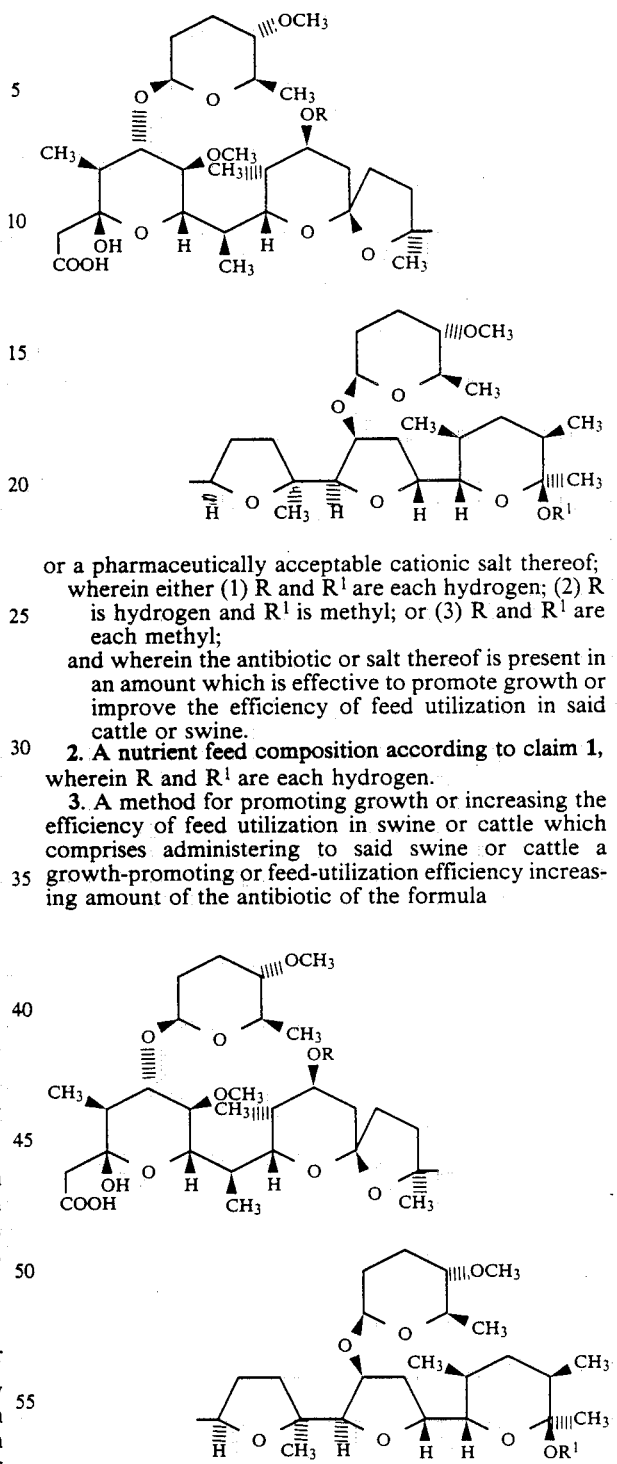

or a pharmaceutically acceptable cationic salt thereof; wherein either (1) R and R$^1$ are each hydrogen; (2) R is hydrogen and R$^1$ is methyl; or (3) R and R$^1$ are each methyl;

and wherein the antibiotic or salt thereof is present in an amount which is effective to promote growth or improve the efficiency of feed utilization in said cattle or swine.

2. A nutrient feed composition according to claim 1, wherein R and R$^1$ are each hydrogen.

3. A method for promoting growth or increasing the efficiency of feed utilization in swine or cattle which comprises administering to said swine or cattle a growth-promoting or feed-utilization efficiency increasing amount of the antibiotic of the formula

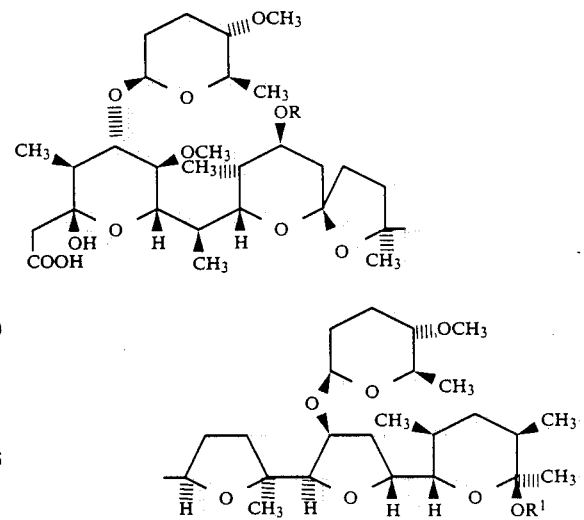

or a pharmaceutically acceptable cationic salt thereof; wherein either (1) R and R$^1$ are each hydrogen; (2) R is hydrogen and R$^1$ is methyl; (3) R and R$^1$ are each methyl.

4. The method according to claim 1 wherein said antibiotic is administered to said swine or cattle by adding said antibiotic to feed ingested by the swine or cattle.

5. The method according to claim 4, wherein R and R$^1$ are each hydrogen.

* * * * *